United States Patent [19]
Beaulieu et al.

[11] Patent Number: 5,821,220
[45] Date of Patent: Oct. 13, 1998

[54] METHOD OF PRODUCING CONCENTRATED NON-BUFFERED SOLUTIONS OF FIBRONECTIN

[75] Inventors: Andre Beaulieu, 4045, Chemin St. Louis, Cap-Rouge (Quebec) G1Y 1V7, Canada; Robert Paquin, St-Jean-Chrysostome, Canada

[73] Assignee: André Beaulieu, Cap-Rouge, Canada

[21] Appl. No.: 767,868

[22] Filed: Dec. 17, 1996

Related U.S. Application Data

[63] Continuation-in-part of Ser. No. 488,253, Jun. 7, 1995, Pat. No. 5,641,483.

[51] Int. Cl.⁶ .................................................... A61K 38/16
[52] U.S. Cl. ............................... 514/8; 530/380; 530/395

[58] Field of Search ...................................... 514/8

[56] References Cited

U.S. PATENT DOCUMENTS 4,341,764  7/1982  Wallace et al. ..................... 424/101

*Primary Examiner*—Frederick Krass
*Attorney, Agent, or Firm*—Manette Dennis; Ostrager, Chong, Flaherty & Onofrio, P.C.

[57] ABSTRACT

Topical gel and cream formulations containing human plasma fibronectin and other wound healing promoters are used for the healing of cutaneous wounds. The formulations provide slow release and increased contact time of fibronectin and of other wound healing promoters to the wound site leading to the effective absorption of the promoters.

6 Claims, 6 Drawing Sheets

METHOD OF PRODUCING CONCENTRATED NON-BUFFERED SOLUTIONS OF FIBRONECTIN

RELATED APPLICATION

This application is a Continuation-in-Part of U.S. application Ser. No. 08/488,253, filed Jun. 7, 1995, now U.S. Pat. No. 5,641,483 for Wound Healing Formulations Containing Human Plasma Fibronectin.

FIELD OF THE INVENTION

The present invention relates to topical dosage forms containing human plasma fibronectin for use in promoting wound healing. In particular, the invention relates to the healing of chronic venous ulcers.

BACKGROUND OF THE INVENTION

Fibronectin is a large glycoprotein containing around 5% carbohydrate. The characteristic form of plasma fibronectin is a disulfide-bonded dimer of 440,000 daltons, each subunit having a molecular weight of about 220,000 daltons. Normally found in plasma at a concentration of about 300 µg/mL, fibronectin is extracted and purified using a method described by Hynes[1]. Plasma fibronectin is also known by various other names, including cold-insoluble globulin, anti-gelatin factor, cell attachment protein, cell spreading factor, and opsonic α2-surface binding glycoprotein. These names reflect biological activities of fibronectin such as cell recruitment, opsonization of particulate debris, and promotion of wound contraction. Reviews on structure and activities of fibronectin have been published elsewhere.

Wound healing is usually divided into three phases: the inflammatory phase, the proliferative phase, and the remodeling phase. Fibronectin has been reported to be involved in each stage of the wound healing process, particularly by creating a scaffold to which the invading cells can adhere. Initially, many mediators, such as fibronectin and fibrinogen, are released to the wound site. Fibronectin promotes inflammatory cells migration into the wound and debris phagocytosis by the monocytes. Thereafter, angiogenesis and reepithelialization take place. At this stage fibronectin exerts chemotactic activity on endothelial cells, and promotes the migration of epithelial cells and fibroblasts onto the basal membrane. Fibronectin also appears to be an essential component of the remodeling phase where it plays a major role in the organization of collagen fibrils. The fibrillar collagen ultimately forms fibrous bundles that greatly enhance the tissue tensile strength, leading to wound closure.

Topically applied plasma fibronectin has been reported as being useful for increasing the rate of wound healing such as in corneal wounds[4,5] and leg ulcers[6]. However, no one has described a suitable topical carrier for use in treating wounds that can ensure the delivery of an effective amount of fibronectin. A major limiting factor in developing an effective topical dosage form of a drug is not only having an active drug, but also having a formulation that allows the passage of the active drug from the carrier (cream, ointment, gel, etc.) into the site of delivery (which in the case of the present invention is a skin wound). Very active drugs, such as growth factors, may have no therapeutic value if the topical formulation does not allow the drug to move from the semi-solid carrier into the wound. Therefore, it would be highly desirable to develop a formulation which would maximize the contact time of the fibronectin with the wound and also control the release of fibronectin to the wound, thereby leading to high absorption values. The present invention provides such a delivery system in the form of aqueous gels and a cream.

SUMMARY OF THE INVENTION

The present invention provides aqueous gel formulations and one cream formulation containing fibronectin and their use for the delivery of an effective wound healing amount of fibronectin to a wound site. The gel formulation comprises a water soluble, pharmaceutically acceptable polymer which is prepared from an effective amount of fibronectin. Examples of such compounds include: vinyl polymers, e.g. polyacrylic acid; polyoxyethylene-polyoxypropylene block copolymers, e.g. poloxamer; and cellulose derivatives, e.g. hydroxypropylcellulose (HPC). The polymer provides viscosity values between 50,000 and 1,000,000 cps at room temperature. The cream formulation is prepared from a commercially available cream base i.e., Schering® base (Schering Canada Inc., Point-Claire, Quebec), which has viscosity values between 60,000 to 80,000 cps at room temperature.

Many advantages are attributed to these dosage forms. Gel and cream formulations of the present invention release effective amounts of a wound healing promoter. Other advantages of gel formulations include: ability to keep the wound moist (which results from the high water content of the gels), ease of application and removal (by washing) from the wound. They also provide a cool feeling when topically applied which can increase patient comfort.

The slow release system of gel formulations of the present invention provides extended release of fibronectin to the wound site. This property of these formulations permits less frequent application to the wound resulting in less disturbance to the healing process. Such formulations maintain fibronectin delivery for up to 24 hours; but according to kinetic data obtained from permeation studies, a "twice a day" therapeutic schedule is a preferred embodiment of the present invention.

Formulation of topical dosage forms intended for the incorporation of fibronectin should respect several quality criteria. All components of the preparation including solvent, gelling agent and preservative should be nontoxic for the wound and compatible with the drug. The final product should promote optimal release of the drug to its site of action, be of adequate consistency to enhance contact time of the drug with the wound and be sterile.

The preferred formulations of this invention can be used with other wound healing promoters having a composition similar to fibronectin, such as proteins of similar size (thrombospondin, laminin, vitronectin, fibrinogen) or smaller size (such as peptides including growth factors).

The preferred formulations can be correlated with the results of evaluating these formulations using an in vitro diffusion cell system consisting of a rigid receptor containing a deepithelialized skin sample, the deepithelialized side facing upwards into a donor compartment and the dermal side facing downwards into a receptor compartment. The deepithelialized skin sample is prepared by removing a 8 µm section from the epidermal surface of the skin using a dermatome (1/10,000 scissor scale) and the dermal side was carefully cleaned of any adhering subcutaneous tissues and/or blood vessels. The receptor compartment is connected to a circulating buffer circuit, with the buffer temperature maintained at 37° C. while the skin surface is at about 32° C. Preferred formulations will have an "Abs value" of greater than 7.8, preferably at least 13.40.

A preferred method of preparing the gels of the invention is to concentrate human fibronectin in demineralized water, which contains the polymerization promoter (NaOH). For higher concentrated fibronectin gels (0.5–1.0%), it is preferable to lyophilize the fibronectin. In both cases, the resulting solutions have a ph of 11.0. It should be apparent to anyone of ordinary skill in the art that, because the pH of solutions formulated in different environments, measured with differing equipment, etc. may vary slightly, the pH value of "11.0" is implicitly understood to embrace "about 11.0". In this manner, it is possible to produce highly concentrated, non-precipitating solutions of fibronectin without using buffers, such as saccharides or stabilizers (e.g., albumin). Concentrated solutions of fibronectin, 2 mg/ml to 10mg/ml, can be reliably achieved using these methods.

The appropriate fibronectin solution is mixed with a concentrated solution of gelling agent. The two solutions are mixed by multiple exchanges under pressure using devices, such as syringes, which do not vigorously agitate the mixture in order to avoid fibronectin precipitation. The mixing devices are connected by an adaptor device.

DETAILED DESCRIPTION OF THE INVENTION

The present invention provides dosage forms that are specially formulated for the therapeutic use of fibronectin as a topical wound healing promoter. The dosage forms selected for topical applications should ideally release large amounts of fibronectin, be sterile and non-toxic for the wound. Several factors such as physico-chemical properties of the glycoprotein as well as clinical utilization criteria must be considered when compounding these formulations.

Among these limitations, the major one relates to the solubility of fibronectin in water which is poor and therefore mitigates against the preparation of concentrated gels or creams. Fibronectin is only slightly soluble in water and may precipitate at concentrations as low as 5 mg/ml in aqueous solution. Its solubility is also affected by ph changes and low temperatures. In the same way, formulations that require the dispersion of polymer powder in the fibronectin solution under agitation cannot be prepared easily since precipitation of the glycoprotein may occur. Under agitation, fibronectin may aggregate and form long mats of insoluble material. Viscosity must be optimal in order to permit a sufficient adherence to the wound as well as good release capabilities.

Temperatures over 60° C., which are frequently required to provide sterile preparations, denature fibronectin. Since a terminal sterilization process cannot be performed on the final product, the preparation of concentrated bases of vehicles without fibronectin is usually unavoidable. Portions of these sterile bases are then diluted with a definite amount of a solution of fibronectin. To achieve adequate dispersion of fibronectin into semi-solid dosage forms, an incorporation step involving agitation is often required which can lead to the precipitation of the drug.

Gelling agents such as Carbopol® carbomer and poloxamer can circumvent this problem since they are sterilized before gelation under a liquid-like, viscous form. A highly concentrated preparation of Carbopol® carbomer is prepared and autoclaved. As described below, the solution of fibronectin which also contains the polymerization promoter (NaOH) is then mixed in syringes with the base of Carbopol® carbomer, building-up the gel during the dispersion of the drug into it. In the case of poloxamer, the polymer is added to the drug solution and allowed to dissolve at 4° C., a temperature at which it maintains its fluid-like aspect. Sterilization of this solution from bacteria is performed at 4° C. using a 0.22 µm filter.

A non-toxic, non-sensitizing preservative compatible with formulation components is added to the dosage form in a preferred embodiment of the invention. All of the above conditions are respected in the preferred dosage forms described in detail as follows.

An effective wound healing amount of human plasma fibronectin for use in the present invention is within the range of about 0.05 to about 1.0%, preferably about 1.0%. Fibronectin is isolated from human plasma by using a gelatin-Sepharose affinity chromatography procedure. In this method, gelatin is covalently coupled to Sepharose 4B after CNBr activation. The binding capacity for human plasma fibronectin provided by this system is >1 mg/ml of gel.

Autologous, homologous human plasma fibronectin or fibronectin obtained from recombinant-DNA technology may be used in the present invention[1,7]. Should homologous plasma fibronectin be used, lots prepared from different donors would have to be tested for atypical antibodies, hepatitis B (HBV), hepatitis C (HCV), human immunodeficiency virus (HIV), human T-cell lymphotrophic virus (HTLV), cytomegalovirus (CMV) and syphilis. These tests have to be performed on donors just prior to the donation and 6 months thereafter. In the meantime, donor plasma must be kept frozen at −20° C. Furthermore, special steps should be taken in order to inactivate potential viruses. An inactivation method using tri (n-butyl) phosphate/Tween-80 or tri (n-butyl) phosphate/Triton X-100 (solvent/detergent method) should be performed on all plasma donations[7,8].

In the gel formulation for topical wound healing, the viscosity may be within the range of 50,000 to 1,000,000 cps, more preferably between 100,000 and 650,000 cps. In the cream formulation, the viscosity may be within the range of 60,000 to 80,000 cps. All viscosity values are in centipoises (cps) as measured using a Brookfield viscometer. Assays were performed at 0.5 rpm and at room temperature.

In one embodiment of the present invention, the gel formulation may comprise 0.25 to 1.0% by weight polyacrylic acid having a molecular weight of about 740,000 to 5,000,000. In a preferred embodiment, the polyacrylic acid is present at 0.35 to 0.75% by weight and has a viscosity of about 350,000 cps. The ph of the polyacrylic acid gel should be within the range of 5 to 8 and more preferably between 6.5 and 7.5. Polyacrylic acid polymer, also known as carbomer, is sold under the trademark Carbopol®. The preferred grade of Carbopol® carbomer is P-934.

In another embodiment, the gel formulation may comprise 18 to 35% by weight polyoxyethylene-polyoxypropylene block copolymer having a molecular weight of about 2,000 to 13,000. In a preferred embodiment, the polyoxyethylene-polyoxypropylene block copolymer is present at 18 to 25% by weight and has a viscosity of about 450,000 cps at room temperature. The Ph of the block copolymer gel should be within the range of 6 to 8 and more preferably between 6.5 and 7.5. Polyoxyethylene-polyoxypropylene block copolymer, also known as poloxamer, is sold under the trademark Pluronic® poloxamer. The preferred grade Pluronic® is F-127 (poloxamer 407).

In a further embodiment, the gel formulation may comprise 1 to 5% cellulose derivative which may be hydroxypropylcellulose (HPC) and has a viscosity of about 25,000 to 150,000 cps. HPC has a molecular weight of about 370,000 to 1,150,000. In a preferred embodiment, the cellulose derivative is present at 2.0 to 4.0% by weight and has a viscosity of about 150,000 cps for HPC. Cellulose derivatives used in the present invention are commonly known as Klucel for HPC. Preferred grade is Klucel-HF.

In a further embodiment, a cream formulation is prepared from a commercially available cream base i.e., Schering base. This cream base (oil in water emulsion) contains ceteth-20, cetostearyl alcohol, chlorocresol, mineral oil, monobasic sodium phosphate, phosphoric acid, sodium hydroxide, water and white petrolatum. The viscosity of the preparation can be modified by varying the content of water and polyethylene glycol.

Formulations of the present invention contain an aqueous phase in combination with a protein and thus are prone to attack by bacteria and fungi. Microbial growth not only spoils the formulation but is a potential toxicity hazard and a source of infection for patients. Even though microbial growth is less likely to be dangerous when it occurs in a topical preparation, it is especially important to preserve topicals which patients have to apply to broken or inflamed skin. Viscosity degradation reported with some polymers when exposed to microbial contamination is also of concern. So, a preservative should be added to the preparation to guarantee long term sterility and stability. The present invention provides gels that comprise a preservative selected from phenol or the para-hydroxybenzoate compounds. In one embodiment, the gel formulation may contain 0.1 to 0.2% by weight chlorocresol, a phenol derivative or 0.01 to 0.3% by weight p-hydroxybenzoate as methyl- and propylparaben. In another embodiment, the cream formulation contains 0.1 to 0.2% by weight chlorocresol.

Stabilizers may be added to the formulation in order to provide stable compositions of fibronectin. They may help to preserve biological activities on a long term basis and may improve water solubility of fibronectin. Among these agents, albumin, disaccharides such as sucrose, and cyclic oligosaccharides such as cyclodextrins are stabilizers of choice. These agents can be used either alone or in combination. Human albumin is preferable in terms of antigenicity and should be free from microbial contamination. Cyclodextrins of the β group (7 glucose units) are of choice and hydroxypropyl-β-cyclodextrin is preferable. The formulation may comprise 0.01 to 0.1% by weight albumin, preferably 0.01 to 0.05%; and/or 0.5 to 5.0% by weight sucrose, preferably 3.0 to 5.0%; and/or 1.0 to 10% by weight hydroxypropyl-β-cyclodextrin, preferably 2.0 to 5.0%.

Some authors have suggested that protease activity in some chronic wounds may cause degradation of adhesion proteins such as fibronectin and prevent cell adhesion necessary for normal wound closure[9]. Metalloproteases and serine proteases have been identified in chronic wound fluid[9,10] and fibronectin has been reported to be highly sensitive to cleavage by proteases[11]. Protection of the integrity of fibronectin may be accomplished by the addition of protease inhibitors in the dosage form. The present invention also provides formulations that may comprise a metalloprotease inhibitor such as EDTA and/or a serine protease inhibitor such as aprotinin (Trasylol®, Miles) with this aim in view. In one embodiment, the dosage form may comprise 0.01 to 1.0% by weight EDTA and/or 1.5 to 45.0 Inh U % by weight aprotinin where 1 Inh U=26 Kallikrein inhibitor units.

Formulations of the present invention can be applied to the wound site by any suitable means which assures that the wound surface will be entirely covered. For example, it can be directly applied to the wound site or used to coat fibers of an absorbent gauze dressing to form a wound healing bandage which may then be placed on a wound.

Examples which follow are intended to illustrate further aspects of the invention and are not to be construed as limiting its scope in any way.

EXAMPLE 1

Isolation of Fibronectin From Human Plasma

1) A sterilization step is mandatory for all homologous plasma donations. In order to inactivate potential viruses, a sterilization procedure using the solvent/detergent method is used. 1% tri (n-butyl) phosphate (TNBP) and 1% Triton X-100 are added to the plasma for 6 hours at 24° C. After that, soybean oil is added to the plasma and allowed to be mixed for at least 30 minutes in order to extract TNBP. Residual Triton will be eliminated by dialysis.
This First Step is Skipped if Autologous Plasma is Used 2) A gelatin-Sepharose 4B column is first prewashed with a Tris-HCl solution in order to equilibrate the gel.

3) The plasma is diluted (1:1) with a Tris-HCl solution and pumped through the column in the presence of phenylmethylsulfonyl fluoride 0.001M (PMSF) for about 15 hours at 4° C.

4) The column is then washed three times in order to elute nonspecifically bound plasma proteins from the gel. All washing steps are performed using a Tris-HCl ph 7.5 solution. A 1M NaCl solution is added to the second washing step to elute contaminants.

5) Elution of fibronectin is carried out by using 0.1M Na acetate + 1M KBr solution.

6) Two dialysis steps are then performed to eliminate contaminants (Triton X-100, Kbr, Na acetate). Dialysis versus PBS and sterile water are respectively done.

7) Solution is concentrated by ultrafiltration under nitrogen pressure.

8) Terminal sterilizing filtration using a 0.22 μm filter is done to warrant sterility.

9) Fractions are aliquoted and frozen at −20° C. until their incorporation into the topical dosage form.

EXAMPLE 2

Polyacrylic Acid Gels

Polyacrylic acid (carbomer) gels (Carbopol® carbomer, BF Goodrich) were prepared. Carbomer is a polymer derived from acrylic acid. It is a high molecular weight polymer (740,00 to 5,000,000) that gelifies when neutralized by strong alkalis (NaOH) or amines (triethanolamine). It forms gels at relatively low concentrations, that is as low as 0.25%, and its viscosity is strongly reduced by the addition of electrolytes.

The preferred grade of polyacrylic acid is Carbopol® 934-P carbomer at concentrations ranging from 0.35 to 0.75% (w/w). Lower concentrations are insufficient to promote adherence to the wound and higher concentrations reduce the release of fibronectin from the gel. Viscosity of polyacrylic acid gels is stable between ph 6 to 8 with a preferred ph range between 6.5 to 7.5. Viscosity is reduced in the presence of strong electrolytes.

A polyacrylic acid gel containing (w/w) fibronectin 0.2%, Carbopol® 934-P carbomer 0.375%, and chlorocresol 0.1% was prepared as follows: chlorocresol (1.0 g) was dissolved in warm (65° C.) deionized water (95 ml) under slow agitation. When the chlorocresol is completely dissolved, the solution is cooled at room temperature while maintaining agitation. Carbopol® 934-P carbomer (3.75 g) was then added, dispersing it slowly on the surface of the solution, and mixed with a paddle type stirrer for about 3 hours. This dispersion was then autoclaved to provide a sterile concentrated gel base (3.75% w/w). A stock solution of fibronectin, 2.2 mg/ml (90 ml), was filtered through a 0.22 μm acetate filter. A polymerization promoter, sodium hydroxide, was added to the fibronectin solution in an amount that will neutralize a 10 g portion of the Carbopol® carbomer 3.75% dispersion, that is 1250 μL of NaOH 3M. The stock solution of fibronectin and Carbopol® carbomer dispersion were mixed into syringes taking care to avoid the introduction of air bubbles and avoiding contamination by working in an aseptic environment, such as under a laminar flow hood. Generally, two syringes are used, and multiple exchanges under pressure are applied. An adaptor device, such as a female luer connection can be used to connect the syringes or other exchange apparatus. Vigorous agitation is minimized in order to avoid fibronectin precipitation. This preparation provides a clear, preserved gel (100 g) of fibronectin free from microorganisms with viscosity of about 350,000 cps.

This gel formulation was applied twice a day on leg ulcers in a pilot study in humans and showed an enhanced rate of wound healing without any adverse effect.

In a preferred embodiment, concentrated solutions of fibronectin, up to at least 10 mg/ml, can be prepared. These solutions can then be used to prepare a concentrated fibronectin gel. In order to prepare the fibronectin gel, the following ingredients must be added in sequence, and are required for the preparation of 10 grams of gel, varying in fibronectin concentration from 0.5 to 1.0%. First, the pH of 9.8 grams of demineralized water is adjusted to 11 with 0.094 grams of NaOH 3M. Lyophilized fibronectin is next dissolved in demineralized water, pH 11, in quantities varying from 0.5 to 1.0 grams. In a final step of the procedure, 0.028 grams of carbomer is added to the mixture.

EXAMPLE 3

Polyoxyethylene-Polyoxypropylene Block Copolymer Gels

Polyoxyethylene-polyoxypropylene block copolymer (poloxamer) gels (Pluronic® poloxamer, BASF Wyandotte) were prepared. The preferred grade of poloxamer is Pluronic® F-127 poloxamer at concentrations ranging from 18 to 25% (w/w). Pluronic® F-127 poloxamer is a low molecular weight polymer (2,000 to 13,000) which exhibits thermal gelation characteristics. Gelation occurs when the concentration reaches 18% poloxamer. The viscosity of poloxamer is proportional to the concentration of the polymer, type of polymer used (molecular weight) and temperature. Fluid at 40° C., the polymer gelifies with increasing temperatures, providing high viscosity values at room temperature. In contrast to Carbopol® carbomer, the addition of ions enhances the viscosity of the preparation.

Concentrated aqueous solutions (20 to 30%) have been reported to show a dramatic increase in viscosity when heated from 4° C. to body temperature. Furthermore, if the ionic strength of the solution is increased, the viscosity is increased more rapidly with rising temperature. Several grades are available but the F-127 grade is the least toxic and gelation can occur at lower concentrations. Gels of poloxamer prepared in this invention are low viscosity solutions at 40° C. and gelify rapidly when they are warmed to body temperature.

A poloxamer gel containing (w/w) fibronectin 0.2% and Pluronic® F-127 poloxamer 20% was prepared as follows: a stock solution of fibronectin 2.2 mg/ml (80 mL) was filtered through a 0.22 μm acetate filter. Pluronic® F-127 poloxamer (20 g) was added to 80 ml of the fibronectin solution and allowed to dissolve without agitation at 4° C. for about 3 days. The resulting solution (100 g) is very liquid-like. Gelation occurs instantly when the solution comes into contact with the wound. A sterilizing filtration process performed at 4° C. could also be applied to the final solution if sterile poloxamer powder cannot be obtained. Viscosity varies from not detectable values at 4° C. to 450,000 cps at room temperature.

EXAMPLE 4

Cellulose derivative gels

Hydroxypropylcellulose (HPC) gels were prepared. In order to illustrate this type of formulations, the preparation of a HPC 3% gel is described as below. The preferred grade is Klucel-HF hydroxypropylcellulose at concentrations ranging from 2 to 4% (w/w).

A gel formulation containing (w/w) fibronectin 0.1%, HPC 3% and parabens was prepared as follows: methylparaben (0.05 g) and propylparaben (0.02 g) were dissolved in warm deionized water (94 ml). HPC powder was sterilized by using a dry heat sterilization process. HPC (6 g) was then dispersed in this solution and allowed to be mixed with a paddle type stirrer for about 3 hours. This provides a sterile concentrated gel base (6% w/w). A stock solution of fibronectin 2 mg/ml (50 mL) was filtered through a 0.22 μm acetate filter. Fibronectin solution (50 ml) was then slowly added to a portion (50 g) of this concentrated base using the low-speed shaft of the stirrer. This provides a preserved gel (100 g) with viscosity of about 150,000 cps.

EXAMPLE 5

Cream Formulation

A cream formulation containing (w/w) fibronectin 0.1%, sterile cream base (Schering® base, Schering) and chlorocresol 0.1% was prepared as follows: a stock solution of fibronectin 2 mg/ml (50 ml) was filtered through a 0.22 μm acetate filter. Fibronectin solution (50 ml) was then added slowly to a portion (50 g) of the cream base using the low-speed shaft of a stirrer. This provides a preserved cream (100 g) with viscosity of about 70,000 cps.

EXAMPLE 6

Kinetics of Release From Different Topical Dosage Forms

The effectiveness of each topical formulation to release fibronectin was evaluated using an in vitro diffusion cell system. Permeation studies were all performed on human breast and abdominal deepithelialized skin samples obtained from breast reduction and abdominal lipectomy surgeries. A 8 μm section was removed from the epidermal surface of the skin using a dermatome (1/10,000 scissor scale) and the dermal side was carefully cleaned of any adhering subcutaneous tissues and/or blood vessels. Deepithelialized human skin was used in order to reproduce the pathological condition met in chronic venous ulcers where the epidermis layer is absent.

The diffusion cell system selected consisted of a rigid receptor containing the skin sample, the deepithelialized side facing upwards into the donor compartment and the dermal side facing downwards into the receptor compartment. The receptor compartment was connected to a circulating buffer circuit. The buffer temperature was maintained at 37° C. while the skin surface was at about 32° C. Each analysis was performed on a 0.64 cm² skin sample using a 100 μl aliquot of $^{125}$I-fibronectin topical formulation specimen. After the experiment, the skin was removed from the diffusion cell, washed 10 times with a 8 ml water volume by wash, and analyzed for its content of radioactivity in a gamma radioactivity counter. The total amount absorbed (dermis + receptor compartment) divided by the dose applied gave the percent absorption. This diffusion cell system has provided excellent reproducible intra- and inter-experimental results.

All dosage forms were made in salt-free solution since viscosity values could have been influenced by the presence of electrolytes. For instance, viscosity values of carbomer gels are reduced in the presence of strong electrolytes in contrast with poloxamer gels which are more viscous when electrolytes are added to the preparation.

Several authors have compared percutaneous absorption studies using in vitro and in vivo techniques to establish the reliability of results using these methods[13,14,15]. These comparisons have clearly shown that in vitro studies can accurately reflect the living state. Statistic analysis applied to our experiments has demonstrated a good correlation value between studies performed on skin obtained from different sources. These data have shown that the origin of the skin did not have any effect on results. percutaneous absorption studies IV: The flow-through diffusion cell. J Pharm Sci 1985: 74:64–67.

Percutaneous absorption studies are usually performed on intact skin and are designed to evaluate the release of a substance from a topical vehicle and its absorption through the major cutaneous barrier, that is the stratum corneum. In cutaneous ulcers, the barrier effect of the stratum corneum is absent. With this pathological condition, only the diffusion from the dermatological vehicle will be a major determinant for the ulterior penetration of the drug into the dermis. The diffusion cell system described above is a suitable in vitro model for cutaneous ulcers.

Kinetic data of the release of fibronectin from various dosage forms were obtained at 4, 12, and 24 hours. Table 1 summarizes these data for t=12 hours. The control consisted of $^{125}$I-fibronectin in phosphate buffered saline solution, pH 7.4. Liposomes used in the Carbopol® 934 P carbomer (1%)+liposomes (15%) formulation (Lipogel) were made from Proliposomes liposomes (Pro-lipo 3090 SH™, Lucas Mayer, France). Cellulose derivatives are identified as CMC for sodium carboxymethylcellulose and HPC for hydroxypropylcellulose. Dermabase® base (Borden, Ltee., Don Mills, Ontario, Canada) and Schering® base are cream bases available on the market and were diluted 1:1 for these experiments. The symbol [ ] refers to components concentration and "Abs value" to the percentage of radiolabelled fibronectin found in the dermis after an exposition time of 12 hours.

TABLE 1

| Formulation | [ ] | Abs value |
| --- | --- | --- |
| Control | | 24.75% |
| Lipogel | | 3.70% |
| Dermabase ® base | (1:1) | 5.80% |
| CMC | 3% | 6.70% |
| Carbopol ® 934 P carbomer + glycerol (Carbogly) | 0.375%/10% | 7.80% |
| Schering ® base | (1:1) | 9.90% |
| Pluronic ® F-127 poloxamer | 20% | 12.80% |
| Carbopol ® 934 P carbomer | 0.375% | 13.40% |
| HPC | 3% | 15.20% |

Figure 1:
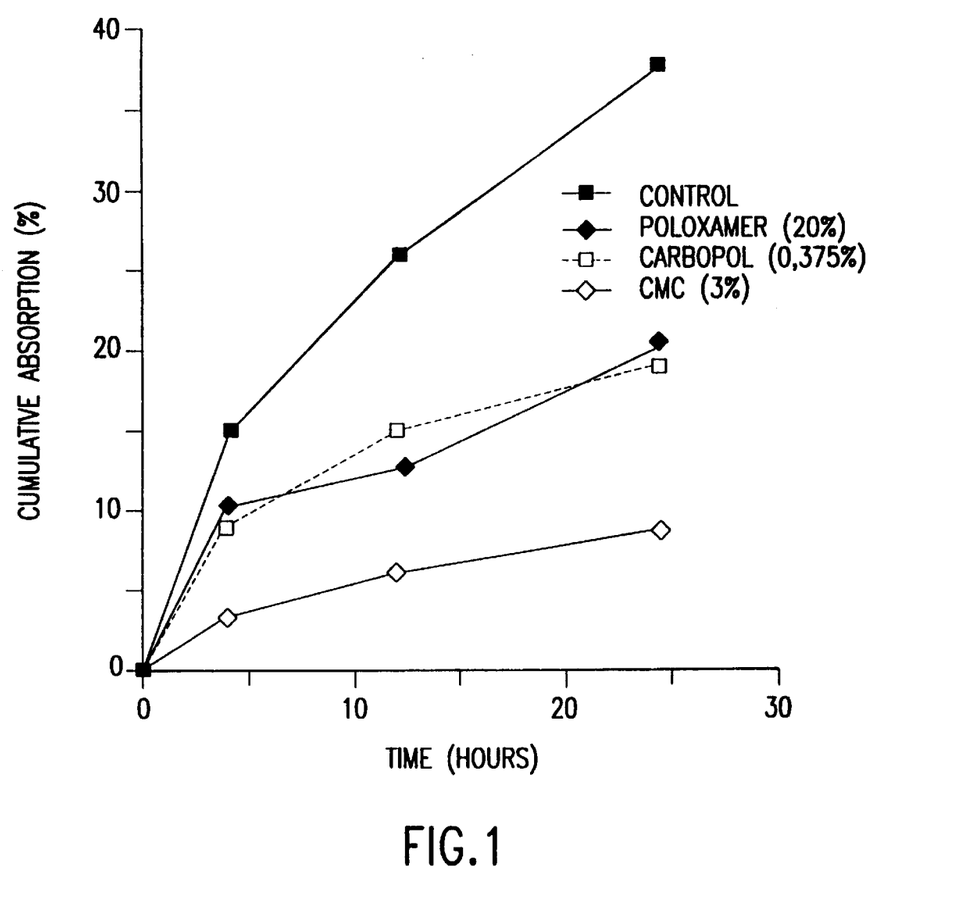
FIG. 1 depicts the cumulative absorption of radio-labelled fibronectin over time from various gel formulations containing Carbopol® P-934 carbomer (0.375%), Pluronic® F127 poloxamer (20.0%), sodium carboxymethylcellulose (CMC 3.0%), and from the control (phosphate buffered saline solution).

FIG. 1 plots kinetic data of three gel dosage forms and control solution over time. From this graph it can be seen that the absorption process tend to be more important between time 0 and 12 hours than between time 12 and 24 hours, suggesting that two applications per day could release more fibronectin than an once a day schedule.

Figure 2:
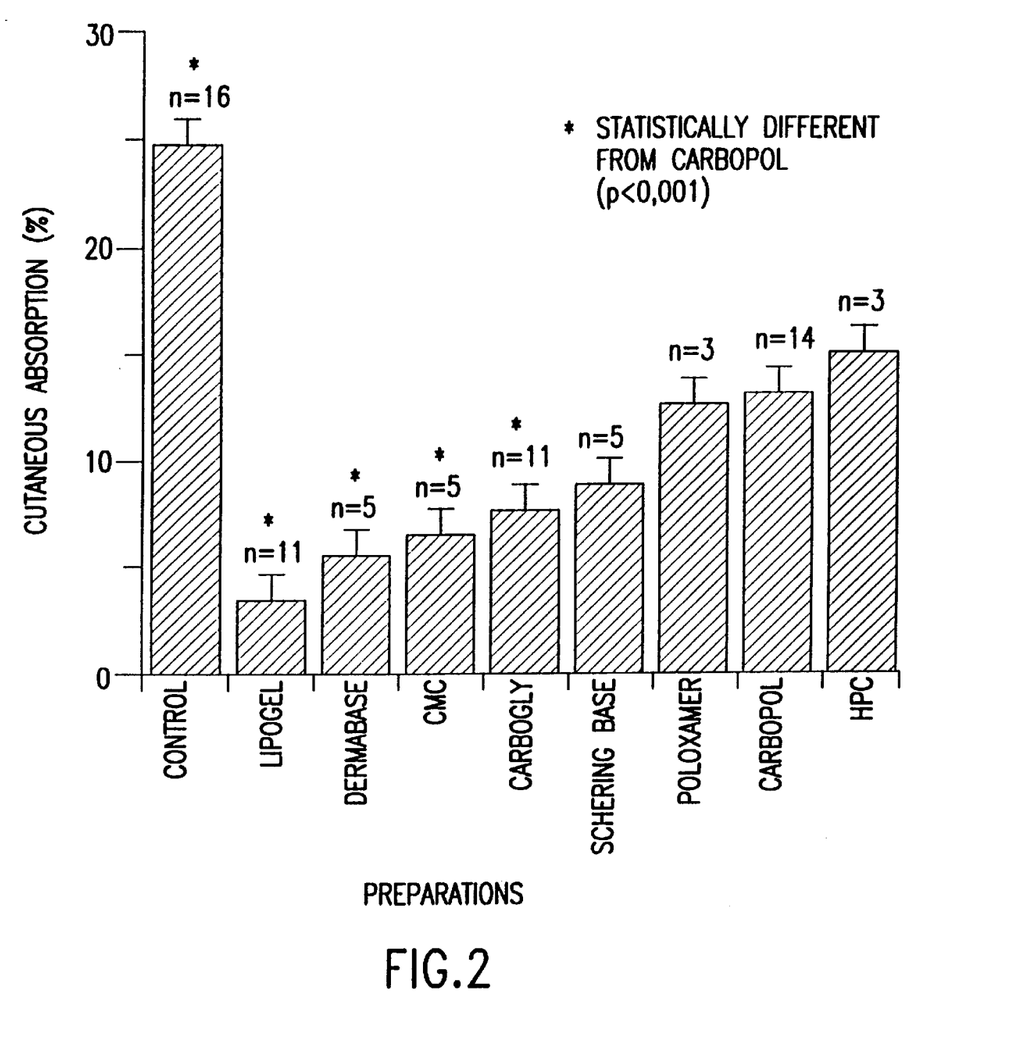
FIG. 2 depicts cutaneous absorption of radio-labelled fibronectin from various dosage forms and from the control (phosphate buffered saline solution) at time =12 hours.

FIG. 2 depicts cutaneous absorption of radiolabelled fibronectin from various dosage forms and from control at time =12 hours. The Dunnett statistic test was used to identify statistically significant differences between Carbopol® carbomer gel and other formulations. This test has also shown significant differences between Lipogel, Carbogly, and Carbopol® carbomer gel, results that can be correlated with those of effectiveness obtained during clinical trials (see Example 8). The efficacy of the Carbopol® carbomer gel formulation is particularly surprising since Carbopol® carbomer gel has a higher degree of viscosity than many of the other formulations studied. Also noteworthy are the difference in Abs value between the Carbopol® carbomer gel and CMC formulations since they both share the same degree of viscosity.

Figure 4:
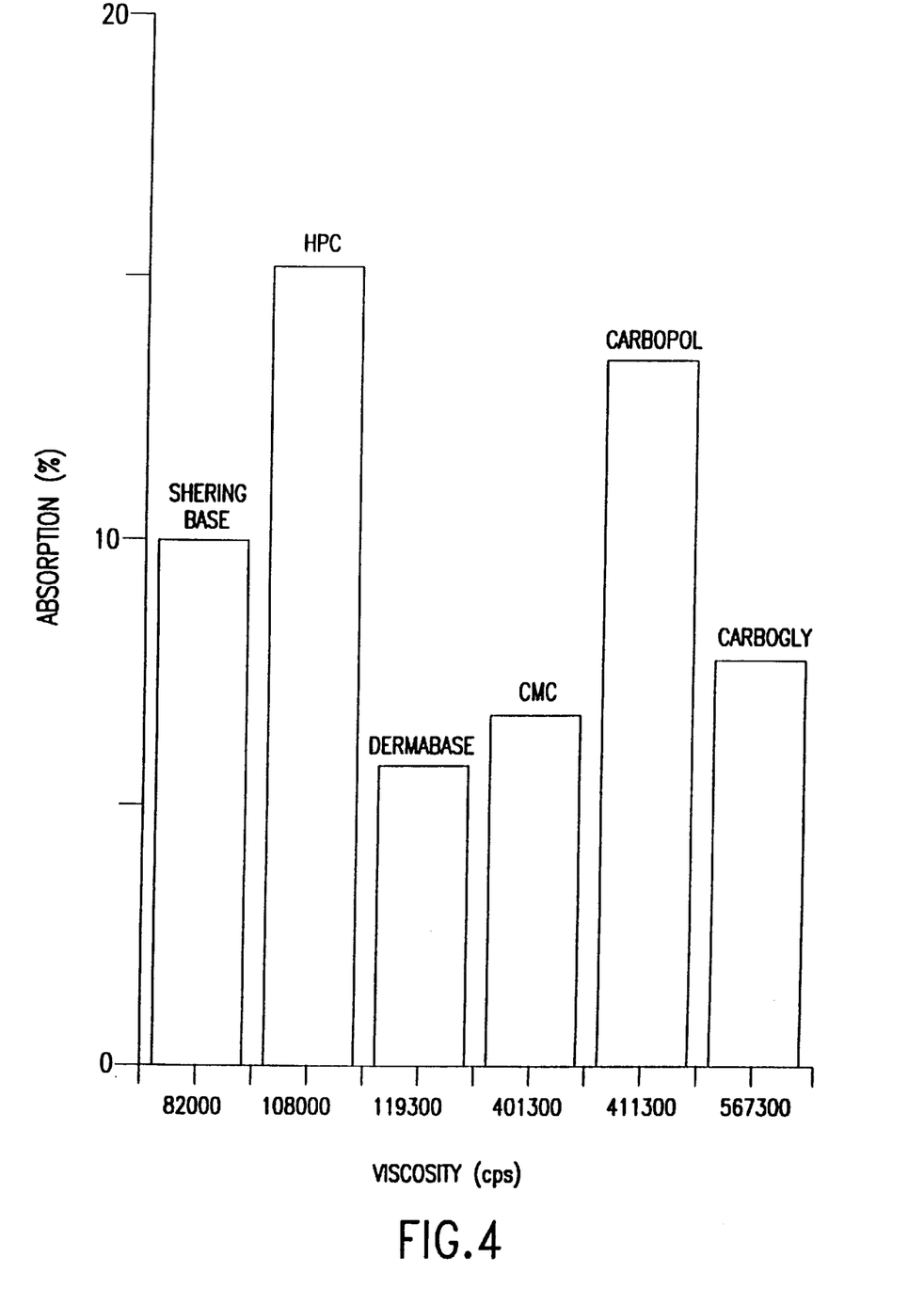
FIG. 4 shows a plot of dermal absorption versus viscosity from different topical preparations.

FIG. 4 show that a clear relationship between viscosity and absorption does not always exist, when considering some of the preparations for which viscosity values were determined. For instance, Dermabase® base which has a relatively low viscosity (119,000 cps) when compared to Carbopol® carbomer gel (411,300 cps) presents poor release capabilities (5.80%) when compared to Carbopol® carbomer gel (13.40%).

Figure 5:
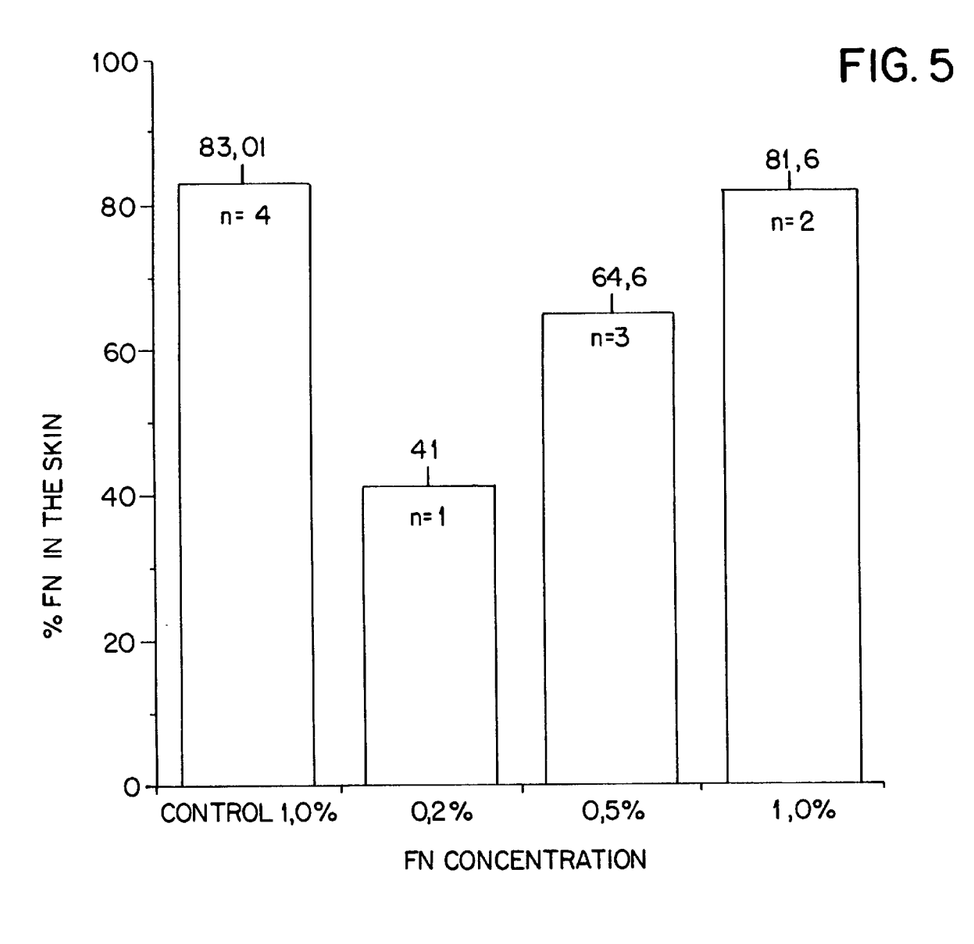
FIG. 5 demonstrates the absorption values in deepithelialized skin using increasing concentrations of fibronectin in carbomer gel containing 0.28% carbomer and from the control (phosphate buffered saline solution).
Figure 6:
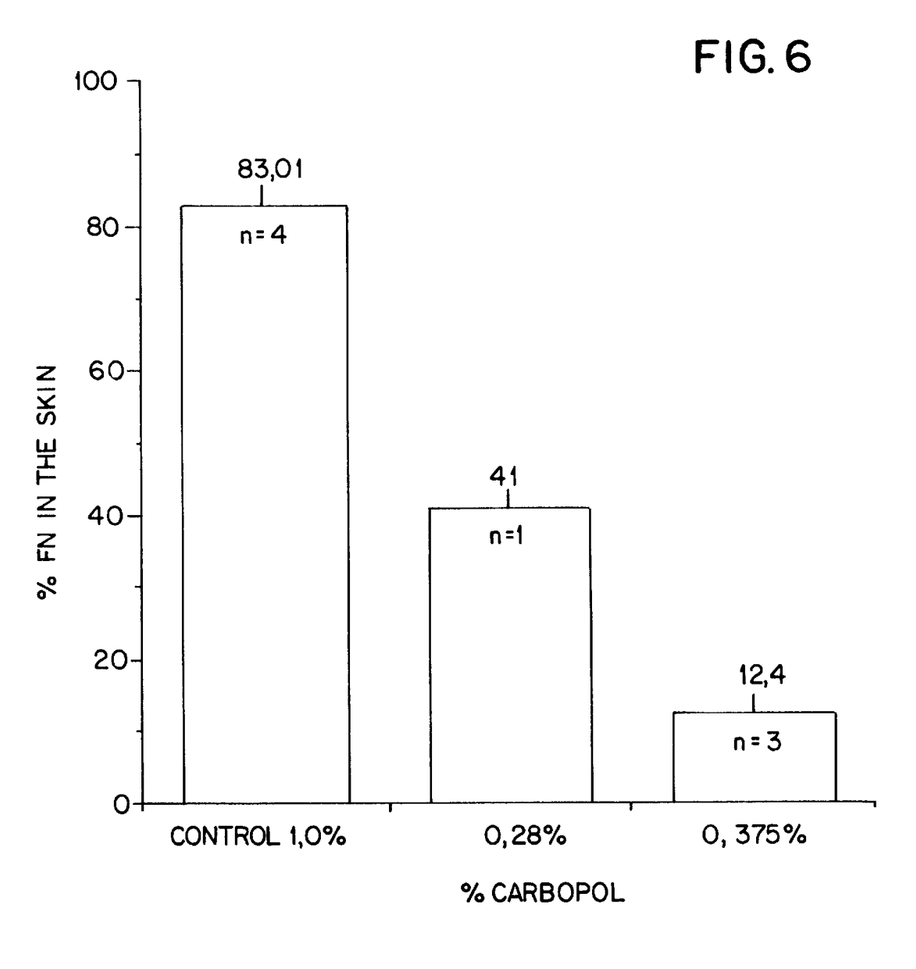
FIG. 6 illustrates the effect of two different concentrations of carbomer on absorption values of fibronectin in deeptithelialized skin. Both carbomer formulations contain 0.2% fibronectin; the control is phosphate buffer solution.

FIG. 5 demonstrates that higher absorption values than 13.40% can be obtained using 0.28% of carbomer and higher concentrations of fibronectin. FIG. 6 directly compares the absorption values obtained in deepithelialized skin diffusion cell system for 0.28% and 0.375% carbomer gels, both of which have 0.2% fibronectin.

In FIGS. 5 and 6, the amount of fibronectin was measured using ELISA procedures. A polystyrene microtiter plate is incubated with 100 μl of different fibronectin samples in 50 mM carbonate/bicarbonate buffer, pH 9.6 at 4° C. overnight. A solution of 5% bovine serum albumin (BSA) in PBS Tween, pH 7.5 is used as a blocking buffer for 30 minutes at 37° C. The plate is washed four times with PBS Tween pH 7.5 and 100 μl of rabbit anti-FN, produced by methods well known in the art, diluted 1/100,000 in 0.5% PBS Tween pH 7.4, are added and the plate is incubated at 37° C. at 1 hour. After rinsing four times with PBS buffer, 100 μL of the goat anti-rabbit horseradish peroxidase conjugated (Jackson Immunoresearch Laboratories, Inc., PA) diluted 1/100,000 in 0.5% PBS Tween pH 7.4, are added and the plate is incubated at 37° C. for 1 hour. Excess conjugate is then thoroughly removed by washing, and the peroxidase fixed to the wells is detected by addition of ABTS (2,2'-azino-bis(3-ethylbenz-thiazoline-6-sulfonic acid) in citrate buffer pH 4.6 containing 0.015% hydrogen peroxide. The reaction is followed by increases in absorbancy at 410 nm as compared with a standard fibronectin peroxidase reaction.

EXAMPLE 7

Stability of Fibronectin in Gel

Figure 3A:
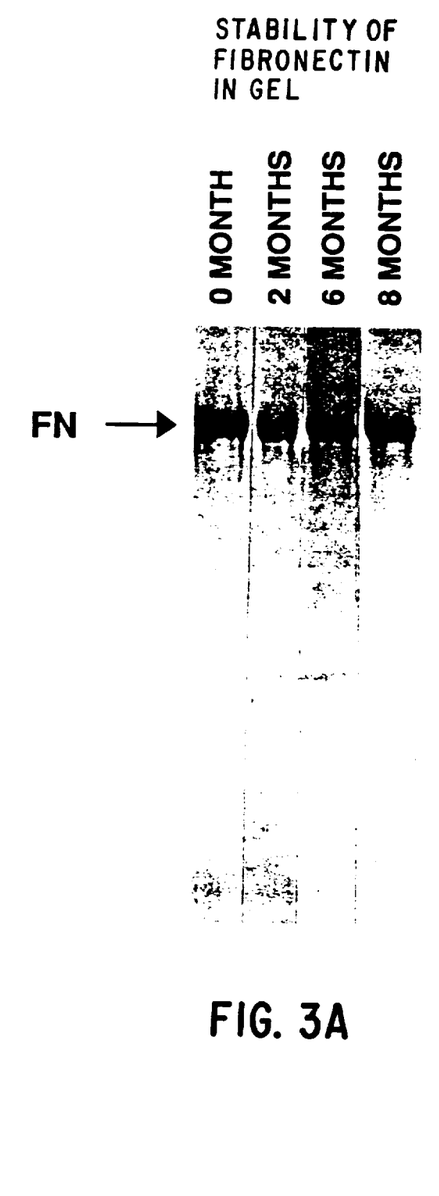
FIG. 3 depicts the electrophoresis of human plasma (FN) incorporated in a Carbopol® carbomer gel (Carbopol® P-934 carbomer 0.375%+chlorocresol 0.1%) after 0, 2, 6, and 8 months. Section A: Recovery of FN after a gelatin-binding test. Section B: Integrity of FN after 240 days of storage in gel at 4° C. It should be noted that in section B, the resolution of the band is affected by the presence of contaminants such as Carbopol® carbomer in the specimen.
Figure 3B:
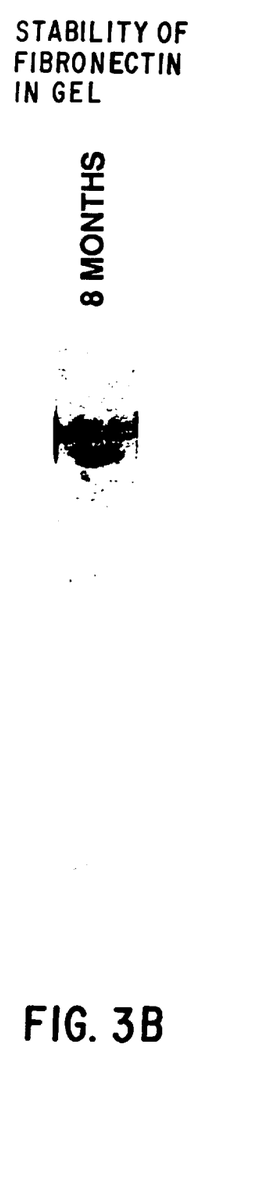

Biological activity and integrity of the macrostructure of fibronectin in gel formulations were evaluated (FIG. 3). Assays were performed on a specimen of gel containing (w/w) fibronectin 0.2%, Carbopol® P-934 0.375% carbomer, and chlorocresol 0.1%. The specimen had been kept at 4° C. for 32 weeks.

Electrophoresis techniques were used in order to determine the integrity of macrostructure of fibronectin in gel. After the specimen of gel was dissolved in 1M NaCl+Tris-HCl pH 7.4 solution, it was allowed to migrate on an 7.5% acrylamide gel according to the method of Laemmli ("Denaturing (SDS) discontinuous gel electrophoresis: Laemmli gel method," pages: 10.2.4–10.2.9, *Current Protocols in Molecular Biology* (1994). Compared with a fresh standard solution (column 0), results showed that close to 100% of the fibronectin can be identified around the 220,000 (column B) band indicating that very little, if any, degradation occurs.

Biological activity was evaluated using an affinity chromatography test. Gelatin-binding is one of these biological activities that can be assessed with relative ease. After a specimen of gel was dissolved in a 1M NaCl solution, a known amount of this viscous solution was placed in an Eppendorf tube in the presence of gelatin-Sepharose 4B and then vortexed. The content was further rinsed with a fresh 1M NaCl solution, centrifuged and the supernatant discarded in order to eliminate contaminants such as Carbopol® carbomer and chlorocresol that came from the dissolution of the gel. Fibronectin was eluted from the gelatin-sepharose 4B using a 1M KBr solution. The fraction collected was allowed to migrate on an 7.5% acrylamide gel according to the method of Laemmli. The band was then evaluated with respect to its content of fibronectin using a densitometric scanning assay. The specimen collected could also be evaluated spectrophotometrically using optical density at wave length λ=280 nm.

Compared with a freshly prepared gel of fibronectin (column 0), it can be seen that a large amount (80%) of fibronectin was recovered from the specimen of gel formulation (column 8 months) indicating that gelatin-binding activity of the glycoprotein can be preserved for a long period of time in this dosage form.

EXAMPLE 8

Clinical Trials: Treatment of Chronic Leg Ulcers

We have conducted five clinical trials (pilot studies) to investigate the usefulness of different dosage forms containing exogenous human plasma fibronectin in the treatment of chronic venous ulcers of lower limbs. In these trials autologous plasma fibronectin was used and patients with ulcers that were resistant to the conventional therapy for at least three months were selected.

The specific objective of the first experiment was to determine the effectiveness of topically applied fibronectin as a wound healing promoter. Seven patients were included in this study and were instructed to "flood" the wound area with a solution of fibronectin, 1 mg/mL (0.1) in PBS (phosphate buffered saline) twice a day. After two months of regular application of that solution, five of these patients presented with a dramatic decrease in their wound size, specifically at least 75% reduction of the integrated surface area.

A second experiment was designed to evaluate the effectiveness of a semi-solid dosage form which contained by weight fibronectin 0.1%, encapsulated in liposomes 15%, which in turn were incorporated in Carbopol® carbomer (1%) formulation known as Lipogel. Hypothesis was that if the contact time of the glycoprotein with the wound could be enhanced, a more rapid decrease in the healing time could theoretically be observed. Six patients were included in this study and they had to apply the formulation to their wound twice a day. None presented a substantial decrease of their wound size during the following three months of regular treatment.

In an attempt to improve the dosage form, an experiment was undertaken to evaluate the therapeutic potential of a topical gel formulation containing (w/w) fibronectin 0.2% incorporated in Carbopol® carbomer 0.375% and glycerol 10% (Carbogly). Glycerol had been added to the formulation in order to take advantage of its humectant effect which could be beneficial to the wound. Eleven patients were recruited for this study and they also had to apply the gel twice a day. Among these patients, 27% had a regression of more than 50% of their wound size after three months of treatment.

Results from the permeation studies may explain, at least in part, what could have occurred in previous experiments. FIG. 2 shows that preparations such as Lipogel and Carbopol® carbomer+glycerol do not lead to high absorption values. In contrast, Carbopol® carbomer 0.375% without glycerol provides significantly higher absorption values (p<0.001). This effect of glycerol was not observed with formulations containing fibronectin above 0.2%. The solution used in the first experiment is identified as the control in this graph. This last preparation provides the highest release capabilities but it does not represent a formulation that could be useful to patients owing to its fluid consistency.

Considering these results, a formulation containing fibronectin 0.2% (w/w) in Carbopol® carbomer 0.375%, without glycerol was investigated in eight patients. According to clinical and permeation studies, this formulation is the preferred carrier using Carbopol carbomer that is available for the use of fibronectin in topical wound healing. Preliminary data showed that 50% of patients studied presented a regression of more than 50% of their wound size within three months of treatment, including two complete responses (100% healing) that occurred within the first eight weeks of treatment.

A fifth clinical trial comprising 40 patients was conducted with the formulation containing fibronectin 0.2% (w/w) in Carbopol® carbomer without glycerol. In this clinical trial, patients were stratified according to duration of the skin ulcer (age of ulcer) at the beginning of the trial. In patients with ulcers of 6 months or less in duration, the formulation containing fibronectin 0.2% (w/w) in Carbopol® carbomer 0.375% without glycerol was not superior to placebo. The placebo was Carbopol® carbomer without glycerol and containing no fibronectin. However, in patients with ulcers of 7 months or more duration at the time of randomization, the fibronectin formulation containing fibronectin 0.2% (w/w) in Carbopol® carbomer 0.375% without glycerol was clearly superior. After 20 weeks of treatment, 58% of the treated group (7/12) had a reduction in wound size of at least 75% after 20 weeks of treatment. Only 25% (1/4) in the placebo group had this beneficial effect. Overall, patients treated with placebo (n=4) deteriorated with a mean wound size increasing by about 60% in size. In the group treated with fibronectin (n=11), the mean wound size decreased by close to 30% after 20 weeks of treatment.

The present invention also provides other formulations that are as useful as this one using the permeation study described in Example 5 as a model system to test the various formulations.

EXAMPLE 9

Case Reports

To illustrate the efficacy of the formulation containing fibronectin and Carbopol® carbomer 934-P 0.375% (w/w), we present two specific cases of chronic venous leg ulcer. These cases are of interest in that the first case was highly resistant to conventional therapy and the second case was a large ulcer. Factors such as duration and surface area have been identified by several authors as playing a major role in the prognosis of the venous ulcer.

Case 1

A 37-year-old woman presented with a ten-year history of chronic venous ulcer of the right lower limb. Her medical history was not significant except for four episodes of phlebitis. The last episode occurred during pregnancy and ultimately resulted in an ulcer. Review of medical treatments that were tried revealed the use of topical antiseptics, elastic stockings, and skin grafting without any positive result.

The patient presented to our clinic with a 1.60 $cm^2$ aching wound. Despite the fact that her ulcer was relatively small, it appeared highly resistant to therapy. Six weeks after starting the application of the gel of fibronectin, a 92% reduction of her wound size could be observed. Complete reepithelialization was noted after a ten-week course of treatment. A follow-up visit scheduled one month later revealed no deterioration in her wound condition.

Case 2

A 39-year-old man presented with a seven-month history of chronic venous ulcer of the left leg. His medical history was not significant except for a saphenectomy of the left lower limb twelve years before. Topical antibiotics were prescribed to the patient without any effect on his wound size.

He presented to our clinic with a 10.5 $cm^2$ ulcer resulting from a local trauma. Lymphedema of the left lower limb was important and a large crusty necrotic layer bordered the wound. The patient's occupation constrained him to remain standing for long periods of time. Although this situation probably worsened his wound condition, it could not be eliminated.

After four weeks of regular application of a placebo gel and normal saline, the wound size increased to 21.5 $cm^2$ as a consequence of local debridement. The placebo gel comprised 0.375% Carbopol® carbomer 934-P, 0.1% chlorocresol, purified water and NaOH to adjust the pH. Active treatment with the fibronectin-containing Carbopol® carbomer gel formulation was begun at this time. Maximum wound size was noted six weeks later (37.5 $cm^2$), revealing a larger ulcer than initially assumed. The wound healing process took place between six to eight weeks and was completed after 31 weeks of active treatment. A follow-up visit scheduled one month later revealed no deterioration in his wound condition.

Although the present invention has been described in relation to particular embodiments thereof, many other variations and modifications and other uses will become apparent to those skilled in the art. It is therefore understood that numerous variations of the invention can be made which are well within the scope and spirit of this invention as described in the appended claims.

REFERENCES

1—Hynes, R. O., Methods for identification of fibronectin (chap. 2, page 12), *IN: Fibronectins* New-York: Springer-Verlag, 1990.

2—Hynes, R. O., Methods for identification of fibronectin (chap. 2, pages 7–23) and Wound healing, inflammation, and fibrosis (chap. 14, pages 349–64), *IN: Fibronectins* New-York: Springer-Verlag, 1990.

3—Brotchie, H., Wakefield, D. Fibronectin: Structure, function and significance in wound healing. Australas J Dermatol 1990; 31:47–56.

4'Nishida, T., Nakagawa, S., Awata, T. et al., Rapid preparation of purified autologous fibronectin eyedrops from patient's plasma. Jpn J Ophthalmol 1982;26:416–24.

5—Phan, T. M., Foster, C. S., Boruchoff, S. A. et al., Topical fibronectin in the treatment of persistent corneal epithelial defects and trophic ulcers. Am J Ophthalmol 1987;104: 494–501.

6—Wysocki, A., Baxter, C. R., Bergstresser, P. R. et al., Topical fibronectin therapy for treatment of a patient with chronic stasis ulcers. Arch Dermatol 1988; 124:175–

7—Edwards, C. A., Piet, M. P. J., Chin, S. et al., Tri (n-butyl) phosphate/detergent treatment of licensed therapeutic and experimental blood derivatives. Vox Sang 1987; 52:53–9.

8—Horowitz, B., Bonomo, R., Prince, A. M. et al. Solvent/detergent-treated plasma: a virus-inactivated substitute for fresh frozen plasma. Blood 1992; 79: 826–31. 77.

9—Grinnell, F., Ho, C. H., Wysocki, A., Degradation of fibronectin and vitronectin in chronic wound fluid: Analysis by cell blotting, immunoblotting, and cell adhesion assays. J Invest Dermatol 1992; 98: 410–6.

10—Chen, W. Y. J., Rogers, A. A., Lydon, M. J., Characterization of biologic properties of wound fluid collected during early stages of wound healing. J Invest Dermatol 1992; 99: 559–64.

11—Berman, M., Manseau, E., Law, M. et al., Ulceration is correlated with degradation of fibrin and fibronectin at the corneal surface. Invest Ophthalmol Vis Sci 1983; 4: 1358–66.

12—Horowitz, B., Chang, M. D. Y., Preparation of fibronectin for therapeutic administration. *IN:* D. F. Mosher (ed.), *Fibronectin,* pages 441–55, San Diego, Academic Press 1989.

13—Franz, T. J., Percutaneous absorption. On the relevance of in vitro data. J Invest Dermatol 1975: 64:190–95.

14—Bronaugh, R. L., Stewart, R. F., Congdon, E. R. et al. Methods for in vitro percutaneous absorption studies. I: Comparison with in vivo results. Toxicol Appl Pharmacol 1982;62:474–80.

15—Bronanugh, R. L., Stewart, R. F., Methods for in vitro percutaneous absorption studies IV: The flow-through diffusion cell. J. Pharm Sci 1985: 74:64–67.

We claim:

1. A method of preparing a non-buffered aqueous solution of human plasma fibronectin comprising the steps of:
   a) adjusting the pH of demineralized water to 11.0 and
   b) adding purified human plasma fibronectin to the demineralized water (pH 11.0) of step a.

2. The method of claim 1, wherein the non-buffered aqueous solution contains at least 2 mg/ml to 10 mg/ml of human plasma fibronectin.

3. The method of claim 1, wherein the fibronectin is lyophilized.

4. A method of preparing a non-buffered aqueous solution of human plasma fibronectin comprising the steps of:
   a) adjusting the pH of demineralized water to about 11.0 and
   b) adding purified human plasma fibronectin to the demineralized water of step a.

5. The method of claim 4, wherein the non-buffered aqueous solution contains at least 2 mg/ml to 10 mg/ml of human plasma fibronectin.

6. The method of claim 4, wherein the fibronectin is lyophilized.

* * * * *